(12) United States Patent
Carnabuci (10) Patent No.: US 11,084,619 B2
(45) Date of Patent: Aug. 10, 2021

(54) SECONDARY PACKAGING CONTAINER AND METHOD FOR HEMODIALYSIS DIALYZERS

(71) Applicant: BELLCO S.R.L., Mirandola (IT)

(72) Inventor: Francesco Carnabuci, Formigine (IT)

(73) Assignee: BELLCO S.R.L., Mirandola (IT)

( * ) Notice: Subject to any disclaimer, the term of this patent is extended or adjusted under 35 U.S.C. 154(b) by 148 days.

(21) Appl. No.: 16/144,100

(22) Filed: Sep. 27, 2018

(65) Prior Publication Data

US 2019/0100352 A1 Apr. 4, 2019

(30) Foreign Application Priority Data

Oct. 4, 2017 (IT) .................. 102017000111328

(51) Int. Cl.

| | |
|---|---|
| B65D 5/49 | (2006.01) |
| A61B 50/30 | (2016.01) |
| B65D 25/04 | (2006.01) |
| B65D 21/02 | (2006.01) |
| B65D 77/04 | (2006.01) |
| A61M 1/14 | (2006.01) |
| B01D 67/00 | (2006.01) |

(52) U.S. Cl.
CPC .......... B65D 5/48038 (2013.01); A61B 50/30 (2016.02); A61M 1/14 (2013.01); B01D 67/0097 (2013.01); B65D 21/0201 (2013.01); B65D 25/04 (2013.01); B65D 77/0413 (2013.01); *A61B 2050/3007* (2016.02); *A61B 2050/3008* (2016.02); *A61M 2209/06* (2013.01)

(58) Field of Classification Search
CPC . A61B 50/33; A61M 2209/06; B65D 5/48038
See application file for complete search history.

(56) References Cited

U.S. PATENT DOCUMENTS

| | | | | |
|---|---|---|---|---|
| 1,880,897 A | | 10/1932 | Drewsen | |
| 5,165,919 A | * | 11/1992 | Sasaki | ............... A61L 33/0011 |
| | | | | 210/500.24 |
| 6,227,370 B1 | * | 5/2001 | Earnshaw | ............... B65D 5/001 |
| | | | | 206/497 |
| 10,201,395 B2 | * | 2/2019 | Doring | ............... B65D 81/266 |

(Continued)

FOREIGN PATENT DOCUMENTS

| | | | | |
|---|---|---|---|---|
| DE | 202011107984 U1 | * | 5/2012 | ........... B65D 5/3685 |
| GB | 2368074 A | * | 4/2002 | ............. B32B 29/08 |
| JP | 2011006082 A | * | 1/2011 | ........... A61M 1/1682 |

OTHER PUBLICATIONS

Extended Search Report from counterpart European Application No. 18198730.6, dated Jul. 22, 2019, 9 pp.

(Continued)

*Primary Examiner* — Mollie Impink
(74) *Attorney, Agent, or Firm* — Shumaker & Sieffert, P.A.

(57) ABSTRACT

The present invention provides a secondary packaging container and a method for packaging hemodialysis dialyzers. The container may comprise a box and at least a packaging division positioned horizontally to fit in the box. The packaging division contains a plurality of housing cavities capable of receiving a plurality of dialyzers. The disclosed secondary packaging container and method protects the integrity of hemodialysis dialyzers during transportation and storage.

19 Claims, 4 Drawing Sheets

(56) References Cited

U.S. PATENT DOCUMENTS

2007/0251858 A1* 11/2007 Martinez ............ B65D 5/48032
                                                                206/703
2010/0193387 A1*  8/2010 Sato .................... A61M 1/1682
                                                                206/438
2015/0298850 A1  10/2015 Cruz
2017/0008663 A1   1/2017 Atsumi
2017/0224430 A1*  8/2017 Doring .................. B65D 85/30
2017/0224433 A1*  8/2017 Doring .................... A61M 1/34

OTHER PUBLICATIONS

Response to Extended Search Report dated Jul. 22, 2019, from counterpart European Application No. 18198730.6, filed Feb. 21, 2020, 6 pp.

* cited by examiner

| Product | Reference Length | Dimension (mm) | | | |
|---|---|---|---|---|---|
| | | L | H | D | |
| | | | | min. | max. |
| HFT03 | Short | 162 | 73 | 32 | 44 |
| HFT05 | | | | | |
| DIDECO DHF02 | | | | | |
| DHF06 | | | | | |
| BLS 803 | | | | | |
| BLS 805 | | | | | |
| AQUAMAX HF 03 | | | | | |
| INFOMED DF 30 | | | | | |
| HF 13 SD | Standard | 306 | 78 | 41 | 44 |
| HF 15 SD | | | | | |
| HF 17 SD | | | | | |
| HF 20 SD | XL | 366 | 78 | 44 | |
| HF 22 SD | | | | | |

FIG. 7

SECONDARY PACKAGING CONTAINER AND METHOD FOR HEMODIALYSIS DIALYZERS

CROSS-REFERENCE TO RELATED APPLICATIONS

This application claims benefit of and priority to Italy Patent Application Serial No. 102017000111328 filed Oct. 4, 2017, the disclosures of each of the above-identified applications are hereby incorporated by reference in their entirety.

FIELD OF THE INVENTION

The present invention relates to a secondary packaging container and a method for packaging and storing a plurality of dialyzers. Specifically, the invention relates to a secondary packaging container and a method for packaging and storing hemodialysis dialyzers.

BACKGROUND

Secondary packaging refers to components intended to protect a product and its primary packaging. Secondary packaging has two central functions. First, secondary packaging plays a vital role in the marketing strategy surrounding the product. Second, secondary packaging groups several products together for ease of handling, transport, and storage. This means that secondary packaging must be able to contain relatively large volumes of primary packaged products, transport the product safely to its retail or consumer destination, and keep the primary packaging in its original condition during storage. Secondary packaging should protect not only the product but also the primary packaging, which often is the packaging most visible to the consumer in retail displays. The most common examples of secondary packaging include cardboard boxes and cardboard/plastic crates.

Hemodialysis dialyzers contain a filtration membrane, such as a hollow-fiber membrane, enclosed in a housing that typically has an elongated shape. Some hemodialysis dialyzers, such as Bellco Phylther hemodialysis dialyzers, have an inlet and an outlet at the opposite ends of the dialyzer, and a pair of Hansen connectors positioned in a direction perpendicular to the elongated housing. The housing and Hansen connectors of a hemodialysis dialyzer are sensitive to vibration and crashing during transportation and storage. Loss of dialyzers due to damages during shipment results in an extra expense to the business.

There is, therefore, a need for a container and a method for packaging hemolysis dialyzers, which will provide a stable secondary packaging configuration to protect a hemodialysis dialyzer's integrity during transportation and storage.

SUMMARY OF THE INVENTION

The present invention addresses this need, by providing a packaging division, a secondary packaging container, related products and related methods.

The invention provides a packaging division capable of housing a plurality of hemodialysis dialyzers in a horizontal way to prevent the collision among the dialyzer pieces. The packaging division allows hemodialysis dialyzers to be efficiently assembled and resistant to harsh transportation conditions. The packaging division may comprise a plurality of housing cavities, each capable of receiving a dialyzer. The housing cavities can be formed by a first separator set and a second separator set, each with a plurality of separators arranged in parallel. The first separator set can be vertically arranged against the second separator set to form the housing cavities.

The present invention further provides a secondary packaging container for packaging hemodialysis dialyzers. The secondary packaging container may include a box and one or more the above-mentioned packaging divisions which are placed horizontally in the box. The box may have one or more side walls and a bottom surface, with the bottom surface connected to an edge of the side wall. The box can be in a configuration of cube, cuboid, cone, cylinder, sphere, or polygonal prism. Each packaging division may be separated from another by an insert. The housing cavities of the packaging division may have a substantially uniformed size which is configured to accommodate the dialyzer.

The box of the secondary packaging container may further comprise a substantially C-flute rippled cardboard layer. Each of the separators of the packaging division may comprise a substantially B-flute rippled cardboard layer. The insert may comprise a substantially M-flute rippled cardboard layer.

Also contemplated is a kit which may include a packaging division mentioned above and one or more dialyzers. A secondary packaging product may comprise one or more kits in which each dialyzer may be a standard-length dialyzer, a short-length dialyzer, or an extended-length (XL) dialyzer. The dialyzers may be placed in the housing cavities respectively, with a Hansen connector of each of the dialyzers orientated upward above the horizontal plane of the packaging division. The Hansen connector of each of the dialyzers may be orientated upward and at a predetermined angle (e.g., 15-60°, 20-30°, 20-25°, about 23°) to a vertical axis.

Also contemplated is a method of packaging hemodialysis dialyzers, such as hollow-fiber hemodialysis dialyzers. The method may involve placing a plurality of dialyzers in a packaging division mentioned above and placing horizontally the packaging division in a box. The box may have one or more side walls and a bottom surface, with the bottom surface connected to an edge of the side wall. The packaging division may comprise a plurality of housing cavities, each capable of receiving a dialyzer. The housing cavities can be formed by a first separator set and a second separator set, each with a plurality of separators arranged in parallel. The first separator set can be vertically arranged against the second separator set to form the housing cavities. Each of the dialyzers can be positioned in the housing cavity of the packaging division with a Hansen connector of each of the dialyzers orientated upward and at a predetermined angle to a vertical axis.

The method of packaging hollow-fiber hemodialysis dialyzers may further comprise placing one or more kits mentioned above separated by an insert. The kit may include a packaging division and one or more dialyzers placed in one or more of the housing cavities of the packaging division respectively. The method may further involve placing the dialyzers in the housing cavities of the packaging division. The housing cavities may have a substantially uniformed size which is configured to accommodate the dialyzers.

In some embodiments, the dialyzers are so placed that the Hansen connector of each of the dialyzers orientated upward above the horizontal plane of the packaging division. The method may further involve placing the dialyzers in the housing cavities of the packaging division. The dialyzer may be a standard-length dialyzer, a short-length dialyzer, and an XL-length dialyzer.

The box as mentioned above which may comprise a substantially C-flute rippled cardboard layer. Each of the separators of the packaging division may comprise a substantially B-flute rippled cardboard layer. The insert may comprise a substantially M-flute rippled cardboard layer.

DETAILED DESCRIPTION

The invention provides a secondary packaging container and a method for packaging hemodialysis dialyzers (e.g., hollow-fiber hemodialysis dialyzers). The secondary packaging container may include a box and one or more packaging divisions which are placed horizontally in the box. The box may have one or more side walls and a bottom surface, with the bottom surface connected to an edge of the side wall. The packaging division may comprise a plurality of housing cavities, each capable of receiving a dialyzer. The housing cavities can be formed by a first separator set and a second separator set, each with a plurality of separators arranged in parallel. The first separator set can be vertically arranged against the second separator set to form the housing cavities.

Definitions

The following definitions are provided to facilitate an understanding of the present invention:

The singular forms "a," "an," and "the" include plural referents unless the context clearly dictates otherwise.

The term "(s)" following a noun contemplates the singular or plural form, or both.

As used herein, the term "comprising" includes, but is not limited to, whatever follows the word "comprising." Thus, use of the term indicates that the listed elements are required or mandatory but that other elements are optional and may or may not be present.

As used herein, "have", "having", "include", "including", "comprise", "comprising" or the like are used in their open ended sense, and generally mean "including, but not limited to."

As used herein, the term "or" is generally employed in its sense including "and/or" unless the content clearly dictates otherwise.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 0-10% of the indicated number. For example, "about 20" may indicate a range of 18 to 22, and "about 1" may mean from 0.9-1.1. Other meanings of "about" may be apparent from the context, such as rounding off, so, for example "about 1" may also mean from 0.5 to 1.4.

As used herein, "box" refers to a three-dimensional structure that can be used to hold or transport a plurality of articles. The box may have one or more side walls and a bottom surface, with the bottom surface connected to an edge of the side wall. The horizontal cross sectional shape of the box body may include, without limitation, circular, elliptical, square, rectangular, and polygonal.

"Horizontal" and grammatical equivalents as used herein generally refer to a position or a direction substantially parallel to the plane of the horizon and at right angles to the vertical.

The phrase "horizontal plane" as used herein refers to a surface substantially parallel to the horizon. For example, the horizontal plane of a packaging division is defined by the bottom edges of the separators in the horizontally-positioned packaging division.

As used herein, "separator" refers to a planar object for maintaining an article out of direct contact with one another. Two sets of vertically arranged separators constitute the packaging division to form a plurality of housing cavities for holding hemodialysis dialyzers.

As used herein, "division" refers to a three-dimensional object comprising a plurality of housing cavities capable of receiving dialyzers. The division may comprise one or more separator sets configured to form housing cavities. The separator sets may be arranged vertically against each other. Each separator set may comprise one or more separators.

The term "insert" as used herein refers to a planar object for separating the adjacent packaging divisions to minimize the direct contact between the packaging divisions. An insert may have substantially the same shape and dimensions as the packaging division, and may additionally include two mutually opposed folded-up handles configured to fit the two sides of the packaging division.

As used herein, "dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

As used herein, the term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly (methyl methacrylate), modified cellulose, or other materials known to those skilled in the art.

As used herein, "hemodialysis" is a technique where blood and a "cleansing fluid" called dialysate are exposed to each other separated by a semi-permeable membrane. Solutes within the permeability range of the membrane pass while diffusing along existing concentration gradients. Water and solutes are also transferred by convection across a pressure gradient that may exist across the dialysis membrane. The dialysate employed during hemodialysis has soluble ions such as sodium, calcium and potassium ions and is not pure water. The sieving properties of the membrane exclude certain solutes above a certain threshold from crossing the membrane. One common sieving property is "albumin sieving." In most situations it is not desirable to remove albumin during renal replacement therapy, as lower blood serum albumin is associated with increased mortality rates.

Figure 7:
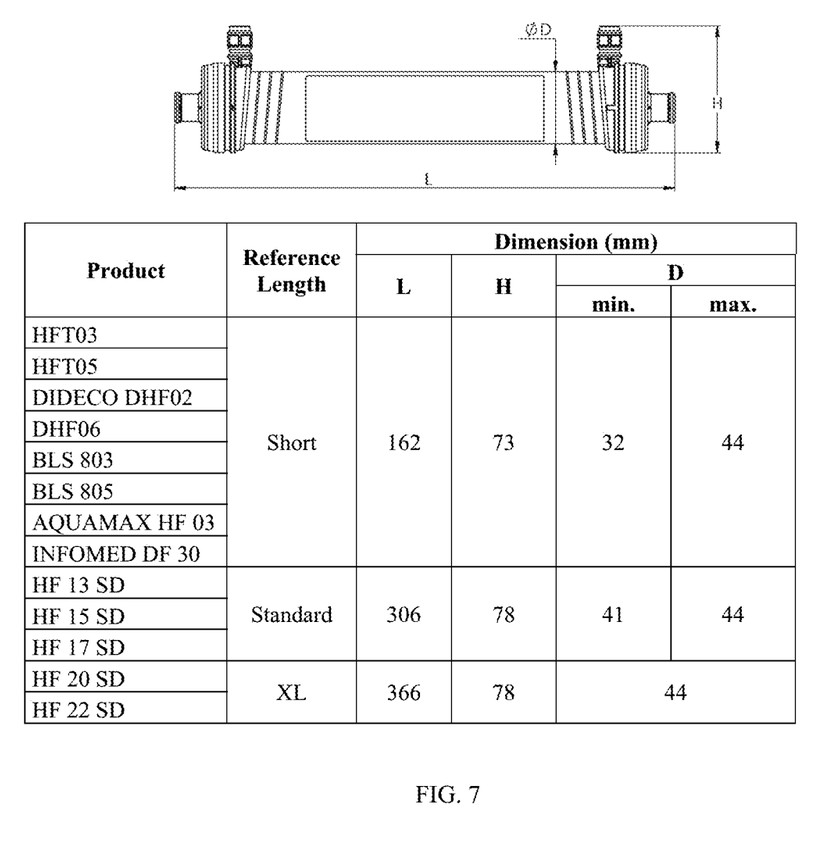
FIG. 7 illustrates measurement of the dimensions (length, height, and diameter) for a member of dialyzers that can be packaged according to the invention.

The term "standard-length dialyzer" as used herein refers to hemodialysis dialyzers having dimensions of about 180-330 mm (length) and about 20-60 mm (diameter), including, without limitation, Bellco Phylther HF13UP, HF15UP and HF17UP hollow-fiber dialyzers. The dimensions of the Bellco standard-length dialyzers are shown in FIG. 7.

The term "short-length dialyzer" as used herein refers to hemodialysis dialyzers having dimensions of about 150-180 mm (length) and about 20-60 mm (diameter), including, without limitation, Bellco dialyzers HFT03, HFT05, DIDECO DHF02, DHF06, BLS 803, BLS 805, AQUAMAX HF 03, INFOMED DF 30 hollow-fiber dialyzers. The dimensions of the Bellco short-length dialyzers are shown in FIG. 7.

The term "XL-length dialyzer" as used herein refers to hemodialysis dialyzers having dimensions of about 330-400 mm (length) and about 20-60 mm (diameter), including, without limitation, Bellco Phylther HF20UP and HF22UP hollow-fiber dialyzers. The dimensions of the Bellco XL-length dialyzers are shown in FIG. 7.

Secondary Packaging Container

Figure 1:
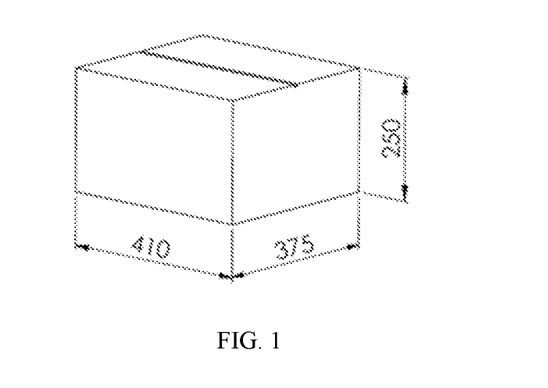
FIG. 1 illustrates a perspective view of a box used in some embodiments of the disclosed secondary packaging container. In some embodiments, the box with a rectangular horizontal cross sectional shape measures about 410 mm long, about 375 mm wide and about 250 mm high.

FIG. 1 illustrates a perspective view showing one embodiment of the invention. Another embodiment of the secondary packaging is integrated by the components shown in FIG. 2, which includes a box 4 with the desired dimensions, one or more packaging divisions 2, one or more inserts 3 to separate a packaging division from adjacent ones, a plurality of dialyzers 6, an instruction manual 1, and a box label 5 attached to the outside of the box.

The container and method for secondary packaging may package different types of dialyzers. The dialyzer may be a hollow-fiber hemodialysis dialyzer. The container and method for secondary packaging may package dialyzers of various sizes. Depending on the number of dialyzers per packaging division and the number of packaging divisions per container, the secondary packaging container is capable of receiving dialyzers with various combinations of length and diameter to match the dimensions of the packaging division and the container. In one embodiment, the dialyzer is a standard-length hollow-fiber hemodialysis dialyzer, including, without limitation, Bellco Phylther HF13UP, HF15UP and HF17UP. In one embodiment, the dialyzer is a short-length hollow-fiber hemodialysis dialyzer, including, without limitation, Bellcodialyzers HFT03, HFT05, DIDECO DHF02, DHF06, BLS 803, BLS 805, AQUAMAX HF 03, INFOMED DF 30. In one embodiment, the dialyzer is a XL-length hollow-fiber hemodialysis dialyzer, including, without limitation, Bellco Phylther HF20UP and HF22UP.

The secondary packaging container of the invention can provide the same external box used for the different types of dialyzers, including the standard-length, short-length, or XL-length hollow-fiber hemodialysis dialyzers. The box may have one or more side walls and a bottom surface, with the bottom surface connected to an edge of the side wall. The horizontal cross sectional shape of the box body includes, without limitation, circular, elliptical, square, rectangular, and polygonal. In one embodiment, the box with a rectangular horizontal cross sectional shape measures about 410 mm long, about 375 mm wide and about 250 mm high, as shown in FIG. 1.

Figure 3:
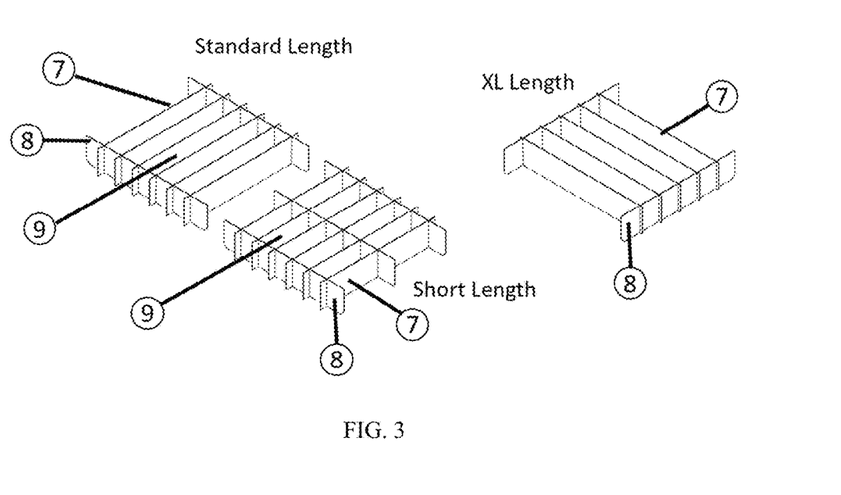
FIG. 3 shows three configurations of the packaging divisions 2 adapted to fit the standard-length, short-length, or XL-length hemodialysis dialyzers. The packaging division may comprise a plurality of housing cavities 9, each capable of receiving a dialyzer. The housing cavities can be formed by a first separator set 7 and a second separator set 8, each with a plurality of separators arranged in parallel. The first separator set can be vertically arranged against the second separator set to form the housing cavities.

In one embodiment, the packaging division 2 for housing the hollow-fiber hemodialysis dialyzers may comprise two separator sets. Each separator set may contain a plurality of separators arranged in parallel. The first separator set 7 can be arranged vertically against the second separator set 8 to form a plurality of housing cavities 9 with a substantially uniformed size configured to accommodate dialyzers. The separated housing cavities reduce the contacts between the dialyzer pieces, and therefore reduce damages of dialyzers and primary packaging during transportation and storage. FIG. 3 illustrates the configurations of the separator sets for accommodating the different types of dialyzers, including the standard-length, short-length, and XL-length hollow-fiber hemodialysis dialyzers. In one embodiment, the packaging division for housing the standard-length hollow-fiber hemodialysis dialyzers includes a first separator set having two separators and a second separator set having seven separators, arranged vertically to hold up to seven standard-length dialyzers per packaging division. In another embodiment, the packaging division for housing the short-length hollow-fiber hemodialysis dialyzers includes a first separator set having three separators and a second separator set having seven separators, arranged vertically to hold up to fourteen short-length dialyzers per packaging division. In yet another embodiment, the packaging division for housing the XL-length hollow-fiber hemodialysis dialyzers includes a first separator set having two separators and a second separator set having six separators, arranged vertically to hold up to six short-length dialyzers per packaging division. Regardless of the different configurations of the packaging divisions for the standard-length, short-length, and XL-length dialyzers, the overall dimensions of the packaging divisions are substantially identical.

Figure 4:
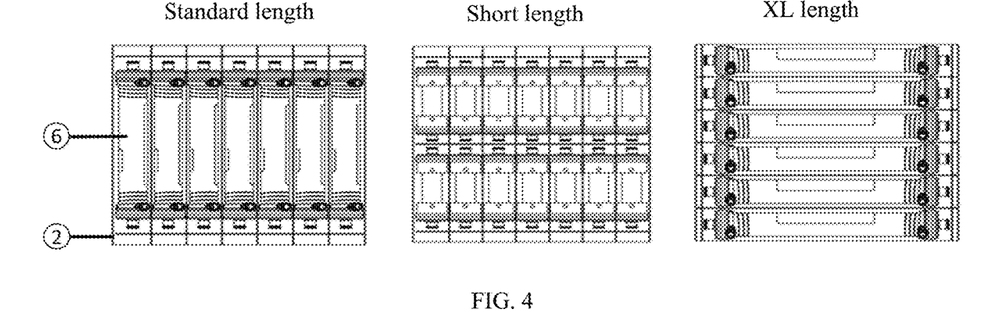
FIG. 4 illustrates top views of the packaging divisions 2 and distribution of the standard-length, short-length, and XL-length dialyzers 6 in the packaging divisions 2. For the standard-length hemodialysis dialyzers with an external diameter of 44 mm or smaller, each packaging division may hold up to 7 units per layer, and up to 21 units in the box when 3 packaging divisions are placed. For the short-length dialyzers with an external diameter of 44 mm or smaller, each packaging division may hold up to 14 units per layer, and up to 42 units in the box when three packaging divisions are placed. For the XL-length dialyzers with an external diameter of 44 mm or smaller, each packaging division may hold up to 6 units per layer, and up to 18 units in the box when three packaging divisions are placed.

The relative orientation of the XL-length dialyzers in the packaging division may differ from those of the standard-length and short-length dialyzers, as shown in FIG. 4. The XL-length dialyzers are aligned with the longer length of the packaging division, whereas the standard and short-length dialyzers are aligned with the shorter length of the packaging division. This does not change the direction which the packaging divisions are fitted in relative to the box. The advantage is that the boxes can be used for shipping both short-length and long length dialyzers by altering the direction they are laid in the box. This also makes it possible to ship the dialyzers of different sizes in the same box, by placing the longer dialyzers on one level, and the shorter dialyzers on another level in the proper orientation. In one embodiment, the secondary packaging container comprises three packaging divisions, with one packaging division having a plurality of standard-length dialyzers, one packaging divisions having a plurality of short-length dialyzers, and the third packaging divisions having a plurality of XL-length dialyzers. In one embodiment, the secondary packaging container comprises a packaging division having a plurality of standard-length dialyzers and a second packaging division having a plurality of short-length dialyzers. In one embodiment, the secondary packaging container comprises a packaging division having a plurality of standard-length dialyzers and a second packaging division having a plurality of XL-length dialyzers. In another embodiment, the secondary packaging container comprises a packaging division having a plurality of short-length dialyzers and a second packaging division having a plurality of XL-length dialyzers.

FIG. 3 depicts a packaging division capable of receiving a plurality of dialyzers. The packaging division may comprise a first separator set 7 and a second separator set 8, each with a plurality of separators arranged in parallel. The first separator set is vertically arranged against the second separator set to form a plurality of housing cavities 9. The housing cavities are capable of receiving a plurality of dialyzers which are positioned in the housing cavity of the packaging division.

Figure 5:
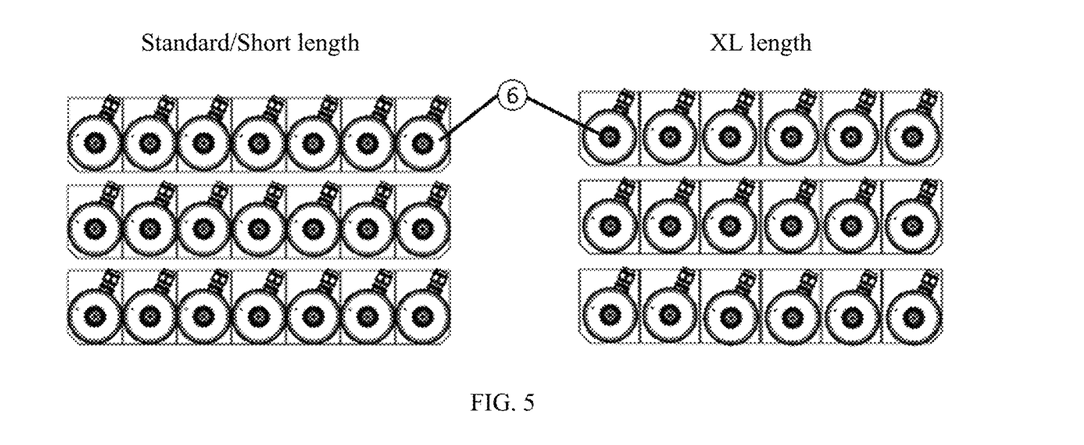
FIG. 5 illustrates side views of the packaging divisions in some embodiments housing the standard-length, short-length, and XL-length dialyzers 6, respectively, where the dialyzers are arranged side-by-side with the Hansen connectors 10 facing upward at a predetermined angle θ to the vertical axis 11.

FIG. 4 shows a kit which may include a packaging division and one or more dialyzers placed in one or more of the housing cavities of the packaging division respectively. A secondary packaging product may comprises one or more kits. FIG. 4 also illustrates top views of the packaging divisions 2 in some embodiments housing the standard-length, short-length, and XL-length dialyzers 6, respectively. FIG. 5 illustrates side views of the packaging divisions in some embodiments housing the standard-length, short-length, and XL-length dialyzers, respectively. The dialyzers are arranged side-by-side with the Hansen connectors facing upward above the horizontal plane of the packaging division and at a predetermined angle θ to the vertical axis 11. The predetermined angle may be any angle smaller than 90 degrees (e.g., 15-60°, 20-30°, 20-25°, about 23°). In some embodiments, the predetermined angle is about 23 degrees. The main reason of this rotation of the dialyzers is to protect the Hansen connectors and reduce potential damages to the primary packaging.

Figure 2:
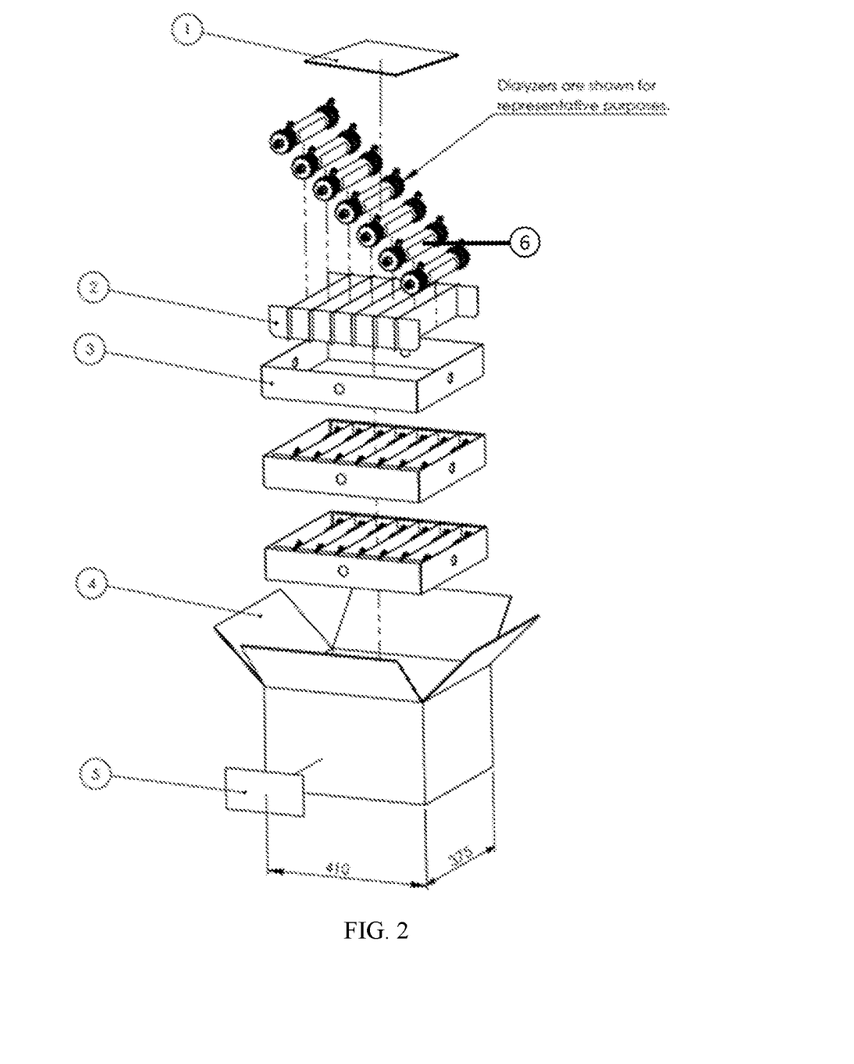
FIG. 2 depicts one embodiment of the secondary packaging integrated by the components, including a box 4 with the desired dimensions, one or more packaging divisions 2, one or more inserts 3 to separate a packaging division from adjacent ones, a plurality of dialyzers 6, an instruction manual 1, and a box label 5 attached to the outside of the box 4.

When packaging one or more packaging divisions, an insert may separate the packaging divisions, as shown in FIG. 2. The insert may have substantially the same size as that of the packaging division. In one embodiment, the insert may have two mutually opposed folded-up handles configured to fit the two sides of the packaging division. When three packaging divisions are packaged, two inserts may be used, with one placed between the first and the second packaging divisions and the other placed between the second and the third divisions.

Figure 6:
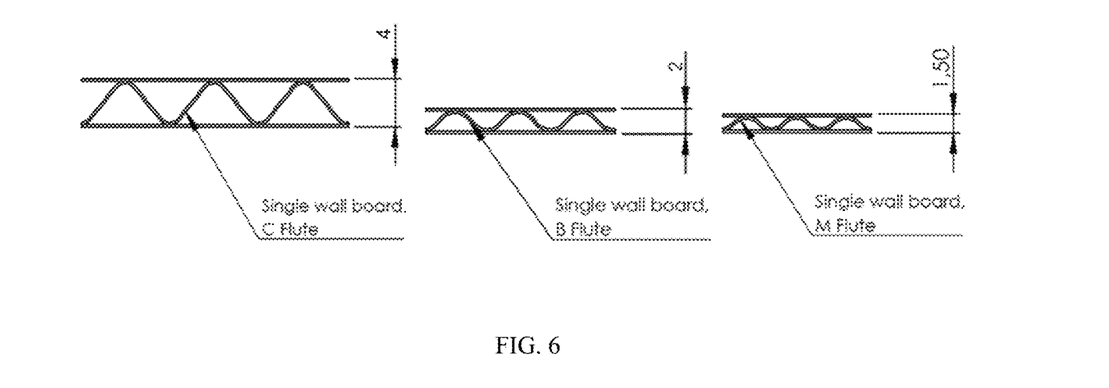
FIG. 6 shows corrugated cardboard materials that can be used for manufacturing the box, the packaging division, and the insert, including a C Flute rippled cardboard (Flute thickness of about 4 mm), a B Flute rippled cardboard (Flute thickness of about 2 mm), and a M Flute rippled cardboard (Flute thickness of about 1.5 mm).

The box, the packaging division, and the insert may be made of the same or different materials and may contain one or more materials. The box may be manufactured from a material capable of providing adequate strength for shipping and storing the dialyzers. The box may be made of cardboard, recycled paper products, a composite material, or other conventional materials. Likewise, the packaging division and the insert may also be made of cardboard, recycled paper products, a composite material, or other conventional materials. In some embodiments, the box, the packaging division, and the insert may be made of one of corrugated cardboard materials, including, without limitation, a C Flute rippled cardboard (Flute thickness of about 4 mm), a B Flute rippled cardboard (Flute thickness of about 2 mm), and a M Flute rippled cardboard (Flute thickness of about 1.5 mm), shown in FIG. 6. In one embodiment, the box comprises one or more substantially C-flute rippled cardboard layer. In one embodiment, each of the separators of the packaging division comprises one or more substantially B-flute rippled cardboard layer. In another embodiment, the insert comprises one or more substantially M-flute rippled cardboard layers.

One particular embodiment according to FIG. 2 comprises a box with a rectangular horizontal cross sectional shape measures about 410 inches long, about 375 inches wide and about 250 high, as shown in FIG. 1. The secondary packaging container further comprises a packaging division configured to substantially fit the size of a standard-length dialyzer, a short-length dialyzer, and an XL-length dialyzer. The dialyzers are placed in the housing cavities of the packaging division, such that the Hansen connector of each of the dialyzers is orientated upward above the horizontal plane of the packaging division and at about 23 degrees. The box of the secondary packing container further comprises one or more substantially C-flute rippled cardboard layer. The packaging division of the secondary packaging container further comprises one or more substantially B-flute rippled cardboard layer. The insert of the secondary packaging container comprises one or more substantially M-flute rippled cardboard layers. The secondary packaging container further comprises three packaging divisions separated by one or more inserts and a box label attached to the box.

Secondary Packaging Method

The present invention also provides a method of packaging hollow-fiber hemodialysis dialyzers. The method may involve placing a plurality of dialyzers in a packaging division and placing horizontally the packaging division in a box. The box may have one or more side walls and a bottom surface, with the bottom surface connected to an edge of the side wall. The packaging division may comprise a plurality of housing cavities, each capable of receiving a dialyzer. The housing cavities can be formed by a first separator set and a second separator set, each with a plurality of separators arranged in parallel. The first separator set can be vertically arranged against the second separator set to form the housing cavities. Each of the dialyzers can be positioned in the housing cavity of the packaging division with a Hansen connector of each of the dialyzers orientated upward and at a predetermined angle to a vertical axis.

In some embodiments, the method may involve placing a plurality of standard-length, short-length, or XL-length hemodialysis dialyzers in the housing cavities of the packaging division. In some embodiments, the method may involve inserting the dialyzer into the housing cavity of the packaging division and then rotating it to one lateral division, such that the Hansen of each dialyzer is orientated upward and at a predetermined angle. In one embodiment, the method may involve inserting the dialyzer into the housing cavity of the packaging division, such that the Hansen of each of the dialyzers is orientated upward above the horizontal plane of the packaging division. In one particular embodiment, the method may involve inserting the dialyzer into the housing cavity of the packaging division, such that the Hansen of each of the dialyzers is orientated upward and at about 23 degrees.

In some embodiments, the method may involve placing one or more packaging divisions, separated by the inserts. When three packaging divisions are placed in the box, two inserts may be used for separating the packaging divisions, with one insert placed between the first and the second packaging divisions and the other insert placed between the second the third packaging divisions.

In some embodiments, the method may further involve placing the dialyzers in the housing cavities of the packaging division, wherein the housing cavities have a substantially uniformed size configured to accommodate the dialyzer.

In some embodiments, the method may involve placing the dialyzers in the box having a substantially C-flute rippled cardboard layer. In some embodiments, the method may involve placing the dialyzers in the housing cavities of the packaging division formed by the separators having a substantially B-flute rippled cardboard layer. In some embodiments, the method may involve placing the dialyzers in the packaging division to form the packaging divisions separated by the insert having a substantially M-flute rippled cardboard layer.

In some embodiments, the method may involve placing one or more packaging divisions in the box which may comprise one or more side walls and a bottom surface, with the bottom surface connected to an edge of the side wall. The horizontal cross sectional shape of the box body includes, without limitation, circular, elliptical, square, rectangular, and polygonal. In one embodiment, the box with a rectangular horizontal cross sectional shape measures about 410 mm long, about 375 mm wide and about 250 mm high, as shown in FIG. 1.

In one particular embodiment, the method includes placing a plurality of dialyzers in a packaging division and placing horizontally one or more packaging divisions in a box. The box with a rectangular horizontal cross sectional shape measures about 410 mm long, about 375 mm wide and about 250 mm high, as shown in FIG. 1. The method further comprises a packaging division configured to substantially fit the size of a standard-length dialyzer, a short-length dialyzer, and an XL-length dialyzer. The dialyzers are placed in the housing cavities of the packaging division, such that the Hansen connector of each of the dialyzers is orientated upward above the horizontal plane of the packaging division and at about 23 degrees. The box of the secondary packing container further comprises one or more substantially C-flute rippled cardboard layer. The packaging division of the secondary packaging container further comprises one or more substantially B-flute rippled cardboard layer. The insert of the secondary packaging container comprises one or more substantially M-flute rippled cardboard layers. The method further comprises three packaging divisions separated by one or more inserts and a box label attached to the box.

Although the present invention has been described in considerable detail referring to certain preferred configurations, other configurations are possible. Therefore, the spirit and scope of the appended claims should not be limited to the description of the preferred configurations contained.

What is claimed is:

1. An assembly comprising:
a plurality of packaging divisions, each packaging division of the plurality comprising a plurality of housing cavities, wherein the plurality of packaging divisions comprises a first packaging division and a second packaging division;
a plurality of dialyzers, at least two dialyzers of the plurality of dialyzers having different lengths, each dialyzer of the plurality being placed in a respective housing cavity of a packaging division of the plurality of packaging divisions,
wherein at least some housing cavities of the first packaging division are each configured to receive a dialyzer having a first length, and at least some housing cavities of the second packaging division are each configured to receive a dialyzer each having a second length different from the first length,
wherein the at least some housing cavities of the first packaging division have a different length than the at least some housing cavities of the second packaging division; and
a box configured to receive the plurality of packaging divisions and the plurality of dialyzers.

2. The assembly of claim 1, wherein the plurality of dialyzers comprises at least two of: a standard-length dialyzer, a short-length dialyzer having a shorter length than the standard-length dialyzer, or an XL-length dialyzer having a longer length than the standard-length dialyzer.

3. The assembly of claim 1, wherein the box comprises a substantially C-flute rippled cardboard layer.

4. The assembly of claim 1, further comprising a first separator set and a second separator set, each of the first and second separator sets having a plurality of separators arranged in parallel, and wherein the first separator set is perpendicularly arranged relative to the second separator set to form the housing cavities of a packaging division of the plurality of packaging divisions.

5. The assembly of claim 1, wherein each packaging division of the plurality of packaging divisions is separated from another packaging division by an insert.

6. The assembly of claim 5, wherein the insert comprises a substantially M-flute rippled cardboard layer.

7. The assembly of claim 1, wherein the housing cavities of a respective packaging division of the plurality of packaging divisions each have a substantially uniform size.

8. The assembly of claim 1, wherein each packaging division comprises a plurality of separators defining a respective plurality of housing cavities, each of the separators comprising a substantially B-flute rippled cardboard layer.

9. The assembly of claim 1, wherein the housing cavities of the first packaging division are each configured to receive the dialyzer having the first length in a first direction and the housing cavities of the second packaging division are each configured to receive the dialyzer having the second length in a second direction different from the first direction.

10. The assembly of claim 1, wherein a Hansen connector of each of the dialyzers is oriented upward and at a predetermined angle to a vertical axis.

11. The assembly of claim 10, wherein the Hansen connector of each of the dialyzers is orientated upward above a horizontal plane of the respective packaging division.

12. A method of packaging hollow-fiber hemodialysis dialyzers, the method comprising:
   placing the dialyzers of the plurality of dialyzers in respective housing cavities of the plurality of packaging divisions of claim 9 such that a Hansen connector of each of the dialyzers is oriented upward and at a predetermined angle to a vertical axis,
   wherein each packaging division of the plurality includes a first separator set and a second separator set, each of the separator sets having a plurality of separators arranged in parallel, wherein the first separator set is perpendicularly arranged relative to the second separator set to form the plurality of housing cavities; and
   placing horizontally the plurality of packaging divisions in the box,
   wherein the box comprises one or more side walls and a bottom surface, wherein the bottom surface is connected to an edge of the side wall.

13. The method of claim 12, wherein the packaging divisions are separated by an insert.

14. The method of claim 13, wherein the insert comprises a substantially M-flute rippled cardboard layer.

15. The method of claim 12, wherein the housing cavities of a packaging division of the plurality have a substantially uniform size.

16. The method of claim 12, wherein the Hansen connector of each of the dialyzers is orientated upward above a horizontal plane of a respective packaging division of the plurality of packaging divisions.

17. The method of claim 12, wherein the plurality of dialyzers comprises at least two of: a standard-length dialyzer, a short-length dialyzer having a shorter length than the standard-length dialyzer, or an XL-length dialyzer having a longer length than the standard-length dialyzer.

18. The method of claim 12, wherein the box comprises a substantially C-flute rippled cardboard layer.

19. The method of claim 12, wherein each of the separators of a packaging division of the plurality of packaging divisions comprises a substantially B-flute rippled cardboard layer.

\* \* \* \* \*